United States Patent [19]

Heil, Jr. et al.

[11] Patent Number: 5,085,218
[45] Date of Patent: Feb. 4, 1992

[54] BIPOLAR MYOCARDIAL POSITIVE FIXATION LEAD WITH IMPROVED SENSING CAPABILITY

[75] Inventors: Ronald W. Heil, Jr., Roseville; Robert W. Wickham, Jr., Harris; Edward D. Kubitschek, Shoreview, all of Minn.

[73] Assignee: Cardiac Pacemakers, Inc., St. Paul, Minn.

[21] Appl. No.: 575,879

[22] Filed: Aug. 31, 1990

[51] Int. Cl.$^5$ .................... A61B 5/0402; A61N 1/05
[52] U.S. Cl. ...................................... 128/642; 128/785
[58] Field of Search ............ 128/642, 784, 785, 419 P

[56] References Cited

U.S. PATENT DOCUMENTS

| | | | |
|---|---|---|---|
| 3,253,595 | 5/1966 | Murphy, Jr. et al. | 128/785 |
| 4,010,758 | 3/1977 | Rockland et al. | 128/785 |
| 4,355,642 | 10/1982 | Alferness | 128/642 |

FOREIGN PATENT DOCUMENTS 3023191 12/1981 Fed. Rep. of Germany ... 128/419 P

*Primary Examiner*—Lee S. Cohen
*Attorney, Agent, or Firm*—Haugen and Nikolai

[57] ABSTRACT

A bipolar lead for use in sensing cardiac depolarization signals and for applying electrical stimulation to cardiac tissue comprises a pair of elongated conductors contained within a lead body, the lead body terminating at its distal end in an enlarged head fabricated from an insulating plastic material. The head has a generally planar surface and projecting perpendicularly from that surface is a corkscrew electrode which is adapted to be screwed into myocardial tissue. Also supported on the planar surface of the head so as to surround the corkscrew electrode is a toroidal electrode formed from helically wound conductive wire. One of the conductors passing through the lead body connects at its distal end to the corkscrew electrode which the other conductor attached to the toroidal electrode. The toroidal configuration of the helically wound wire provides substantially increased surface area when compared to a flat disk electrode and, moreover, offers the ability of tissue to grow into the interior regions of the toroidal electrode for improved anchoring, higher amplitude of the sense depolarization signals and a higher slew rate for the signal. Another feature of the invention involves filling the interior of the hollow torus structure with a wool-like material formed from platinum or other inert conductive material for even further increasing the amount of electrode surface in contact with tissue.

7 Claims, 1 Drawing Sheet

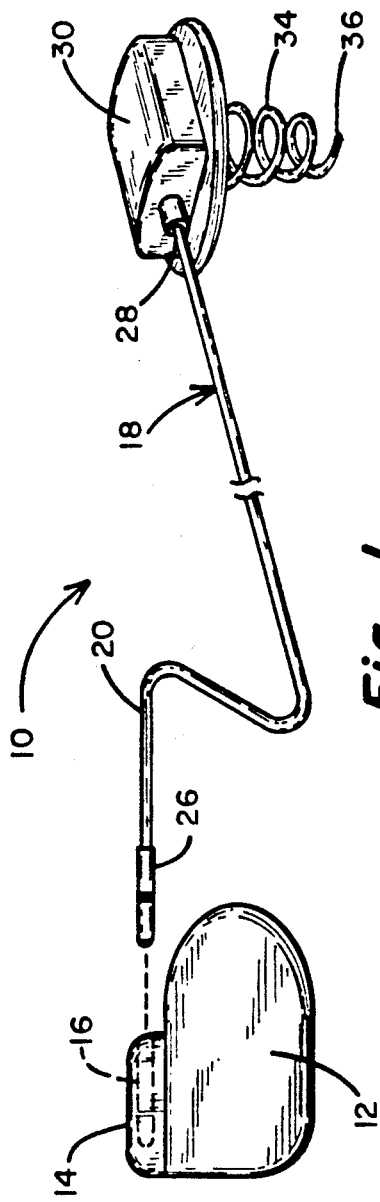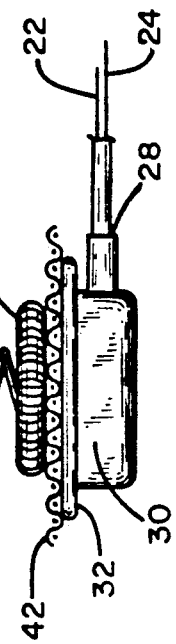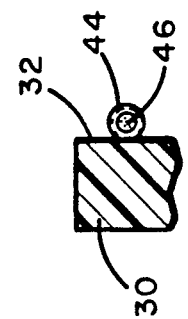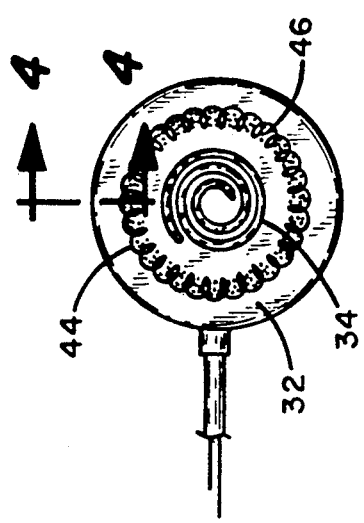

BIPOLAR MYOCARDIAL POSITIVE FIXATION LEAD WITH IMPROVED SENSING CAPABILITY

BACKGROUND OF THE INVENTION

I. Field of the Invention

This invention relates generally to pacing and sensing leads for use with implantable cardiac stimulators, such as pacers and automatic implantable cardiac defibrillators (AICD), and more particularly to a bipolar screw-in type myocardial electrode system offering improved performance over prior art designs.

II. Discussion of the Prior Art

In the U.S. Pat. No. 4,010,758 to Ronald H. Rockland et al and entitled "Bipolar Body Tissue Electrode", there is described a myocardial screw-in bipolar tissue stimulating lead comprising a pair of elongated flexible conductors insulated from one another and extending from a proximal connector to an enlarged electrode supporting head at the distal end of the lead. Projecting outwardly from the head structure is a rigid helix formed from wire and which resembles a corkscrew. Surrounding the helical electrode is an apertured disk, resembling a common flat-washer, but of a suitable electrode material. The helix extends through the opening in the disk in non-contacting relationship. In use, it is intended that the Rockland electrode be screwed into epicardial tissue to the point where the flat disk electrode abuts the surface of the myocardium.

The lead described in the Rockland patent is intended strictly for stimulating cardiac tissue. That is to say, the proximal connector is intended to be coupled to a pulse generator, such as an implanted pacemaker which then functions to deliver a stimulating voltage between the corkscrew electrode and the surrounding disk electrode to the tissue located therebetween. No mention is made in the patent of using that arrangement as a sensing electrode whereby cardiac depolarization signals may be picked up and delivered to the implantable pacemaker for controlling the operation thereof.

In prior art, AICD systems of the type manufactured and sold by Cardiac Pacemakers, Inc. (applicant's assignee), it has been the practice to often utilize two monopolar positive fixation leads, e.g., corkscrew tips cooperating with myocardial tissue, for sensing ECG signals produced upon depolarization of that tissue and using the resulting signals, so detected, in determining whether normal sinus rhythm, tachycardia or ventricular fibrillation is in progress whereby the implanted pulse generator can be commanded to apply an appropriate shock or other stimulation to the heart over separate electrodes to restore sinus rhythm. It is also most important to proper operation of an AICD system that the sensing apparatus recover substantially instantaneously from a previous shocking episode whereby the pulse generator circuitry can determine whether defibrillation has, in fact, taken place or whether it will be necessary to recharge the device's capacitors in anticipation of the need for another shock to be administered. It is also known that antitachycardia pacing schemes may be employed to electrically treat tachycardia. Also, the heart may require short term back-up pacing following conversion attempts. In both cases, the electrode configuration used does not necessarily have to be designed or optimized for long term, chronic stimulation. In such cases, a lead designed for sensing may be suitable for delivery of these short term therapies.

In that the insertion of a positive fixation corkscrew electrode into the myocardial tissue is, at least, modestly traumatic, it is desirable, where possible, that only a single puncture be made. Thus, a bipolar electrode structure, rather than the use of two monopolar electrodes, is advantageous. To those familiar with the literature, it is known that a small surface area electrode favors pacing performance while a large surface area electrode favors sensing performance. These conflicting requirements, most recently pointed out by Sinnaeve, et. al., (PACE, volume 10, 1987, p. 546–554), makes the design of a single electrode, optimized for both purposes, especially difficult.

SUMMARY OF THE INVENTION

The present invention is deemed to be an improvement over the electrode arrangements disclosed in the Rockland U.S. Pat. No. 4,010,758. Specifically, by substituting a toroidal helically wound wire for the flat apertured disk electrode in Rockland, it is found that surprising performance advantages result. Specifically, the use of helically wound torus with the corkscrew electrode permits substantial tissue ingrowth between contiguous turns immediately following the implantation thereof whereas in the prior art structure, as disclosed in the Rockland patent, it may take several weeks for the electrode/tissue interface to mature. Because of the possibility for intimate tissue ingrowth into the interstice of the helically wound wire torus electrode, more stable cardiac depolarization signals can be monitored. Not only that, the slew rate for the cardiac depolarization signals being sensed is significantly higher than can be obtained using the Rockland electrode structure with its flat non-porous disk electrode which contacts the myocardial tissue.

In accordance with a further feature of the present invention, it is possible to fill the interior of the torus with a multiplicity of fine metallic fibers to form a fabric resembling steel-wool. With the myriad of porous openings afforded in this wool-like material, even greater surface area is made to engage the ingrowing tissue, thus enhancing the lead performance.

The bipolar, positive fixation, myocardial screw-in lead of the present invention comprises an elongated flexible plastic lead body having a proximal end and a distal end. First and second elongated flexible conductors extend through the lead body from the proximal end to the distal end in a way that insures that the two conductors are insulated from one another. An enlarged insulating electrode supporting lead head is affixed to the distal end of the lead body and has a generally planar exterior surface. The rigid helix or corkscrew electrode has one end supported by the lead head and it projects perpendicularly to the planar exterior surface and is electrically connected to the first conductor. The second conductive electrode of the bipolar pair is a generally rigid toroidal winding of generally circular cross-section and it is supported on the planar exterior surface of the lead head so as to surround the corkscrew electrode. The toroidally wound electrode is electrically joined to the second conductor in the lead body.

In use, the lead head may be appropriately gripped with an insertion tool which supports the elongated conductors in such a fashion that the helical tip or corkscrew can be rotated and screwed into tissue to the point where the annular helix also contacts myocardial tissue but without torquing the elongated conductors. In this way, the corkscrew remains implanted in the myocardial tissue when the electrode supporting head is released from the tool.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

FIG. 1 is a perspective view of a bipolar myocardial screw-in lead in accordance with a first embodiment of the invention;

FIG. 2 is an enlarged side view of the distal end portion of the lead of FIG. 1;

FIG. 3 is a plan view of the electrode head in accordance with a second embodiment; and FIG. 4 is a cross-sectional view taken along the line 4—4 in FIG. 3.

DESCRIPTION OF THE PREFERRED EMBODIMENT

Referring now to FIG. 1, there is indicated generally by numeral 10 apparatus for sensing ECG potentials developed during depolarization and repolarization of the cardiac tissue and stimulating cardiac tissue. The system is seen to include an implantable pulse generator 12 which, for purposes of this invention, may be a low power stimulator of the type commonly used for pacing patients having bradycardia or, alternatively, it may comprise any one of a number of types of electrical stimulators now used in treating episodes of tachycardia or may also be an implanted automatic implantable cardiac defibrillator. The pulse generator 12 includes a molded plastic header 14 having at least one bore 16 formed therein for receiving a proximal lead terminal therein. The sensing and stimulating lead in accordance with the present invention is indicated generally by numeral 18 and is seen to include an elongated flexible plastic lead body 20 which may be formed from materials such as silicone rubber, polyethylene, polyurethane, polypropylene or other known materials which have been used for a number of years in fabricating pacing leads. Routed through the lead body 20 are a pair of conductors 22 and 24 (FIG. 2) which are terminated at their proximal end by a terminal pin 26 which is designed to be inserted within the bore 16 of the stimulator 12. While in FIG. 1, an in-line terminal 26 is illustrated, those skilled in the art can appreciate that separate terminal pins can be associated with each of the conductors 22 and 24 so as to fit into separate bores in the header 16.

Affixed to the distal end 28 of the lead body is an enlarged electrode supporting head 30 which is preferably molded or otherwise formed from plastic and which includes a generally planar surface 32 (FIG. 2).

Extending perpendicularly from the planar surface 32 is a helix 34 formed from a generally rigid wire and terminating in a sharpened tip 36. The electrode 34 may be covered over a portion of its surface with an insulating coating 38 so that only a small segment proximate the tip 36 remains exposed bare metal.

The structure thus far described is substantially identical to the same arrangement illustrated in the aforereferenced Rockland patent. In accordance with the present invention, however, the flat circular disk electrode in the Rockland device is replaced with a toroidally wound wire electrode 40 which is appropriately boned with a suitable medical grade adhesive or by some other means to the electrode supporting surface 32 of the head 30. The toroid 40 is positioned so as to surround the corkscrew electrode 34 in on-contacting relationship. In the arrangement shown in FIGS. 1 and 2, the toroid 40 has its adjacent convolutions abutting one another and because the convolutions are formed from conductive wire having a circular cross-section, the electrode surface will be non-planar and somewhat corrugated in appearance. This results in a significantly greater area of surface contact with tissue when contrasted with a flat apertured disc It has been determined that a ratio of the surface area of the electrode 40 to that of the tissue subtended by the electrode lies in the range of from 5 to 20.Moreover, the minute spaces present between abutting convolutions allow for improved tissue migration and ultimate anchoring of the annular electrode to the myocardial surface which it abuts when the open-turn helical electrode 34 is advanced, by screwing, into the tissue. As is known in the prior art, a dacron screen as at 42 may also be affixed to the lead head 30 to enhance anchoring, via tissue ingrowth. Furthermore, the enhanced anchoring due to the presence of this tissue ingrowth would reduce any relative motion between the annular electrode and the heart tissue and therefore reduce or eliminate erosion of the tissue by the electrode.

Referring next to FIGS. 3 and 4, an alternative embodiment of the invention comprises a lead structure again having a corkscrew-shaped helical electrode 34 projecting normally from a planar surface 32. Surrounding the rigid helix 34 is a helically wound bare wire coil whose adjacent turns are non-abutting and thus resemble a stretched coil spring. This electrode is identified by numeral 44 and stuffed within its interior is a filamentary mass which resembles steel-wool in its appearance. The filaments may be platinum, a platinum alloy or other metal commonly used in fabricating implantable body contacting electrodes. The distance between adjacent turns on the helically wound wire electrode 44 is sufficient to allow exposure of the conductive filaments comprising the mass 46 to tissue ingrowth and intimate contact with body fluids while preventing migration of the material 46 outside of the bounds defined by the convolutions of the helically wound wire 44. The partial cross-sectional view of FIG. 4 is helpful in visualizing the composite annular electrode heretofore described. The filamentary mass may also be needed to increase the surface area of the electrode as some surface area may be covered during some assembly processes, such as gluing or welding. Increased surface area can also be achieved by well-known methods of roughening, texturizing, and or "blacking" as done to platinum. This can be incorporated on either or both of electrodes 34 and 40.

It can be seen, then, that the present invention provides a single bipolar sutureless myocardial lead which can be used with either a bradycardia pacemaker or with a AICD device for sensing cardiac rate. Being a bipolar device, it replaces the two unipolar sutureless myocardial leads commonly used with implantable defibrillating systems. By replacing the two leads by a single device, the implant procedure is simplified while trauma to the heart is reduced. Moreover, the bipolar lead may only require a single pin type proximal connector, thus freeing up space on the header of the pulse generator.

Still further, the concentric nature of this electrode configuration makes placement of this lead on the surface of the heart less critical than the two leads. This is due to the fact that sensing by a concentric device is essentially independent of the direction of the cardiac depolarization wavefront. This is not the case for sensing by two unipolar devices.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A bipolar, positive fixation myocardial screw-in lead comprising:
   (a) an elongated flexible plastic lead body having a proximal end and a distal end;
   (b) first and second elongated flexible conductors extending through said lead body from said proximal end to said distal end, said first and second conductors being insulated from one another within said lead body;
   (c) an enlarged insulating electrode supporting lead head affixed to said distal end of said lead body, said lead head having a generally planar exterior surface;
   (d) a first conductive, generally rigid, helically-shaped electrode of open convolutions having one end supported by said head and extending normally to said planar exterior surface and terminating in a free end and being electrically connected to said first conductor;
   (e) a second conductive, generally rigid, helically-shaped electrode of substantially open but closely spaced convolutions sufficient to allow tissue ingrowth and formed as an annulus of generally round cross-section and supported on said planar exterior surface surrounding said first electrode, said second electrode being electrically connected to said second conductor.

2. The bipolar lead as in claim 1 wherein said second electrode comprises a conductive wire of circular cross-section wound as a coil to thereby present a corrugated surface contour.

3. The bipolar lead as in claim 2 wherein said first electrode is partially covered with an insulating material except proximate said free end.

4. The bipolar lead as in claim 3 and further including connector means electrically connected individually to said first and second conductors for connecting said lead to implantable cardiac tissue stimulating apparatus.

5. The bipolar lead as in claim 4 wherein the ratio of the surface area of said second electrode to the tissue subtended is in the range of from about 5 to about 20.

6. The bipolar lead as in claim 2 and further including a mass of conductive fibers contained within the interior of said coil.

7. The bipolar lead as in claim 2 wherein one of said first and second electrodes is surface treated to increase the effective surface area thereof.

* * * * *